(12) United States Patent
Hendi

(10) Patent No.: US 6,441,174 B1
(45) Date of Patent: Aug. 27, 2002

(54) PROCESS FOR PREPARING BIS (HYDROXYMETHYL) PERYLENETETRACARBOXIMIDE

(75) Inventor: Shivakumar Basalingappa Hendi, Newark, DE (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/008,913

(22) Filed: Dec. 6, 2001

Related U.S. Application Data

(62) Division of application No. 09/428,101, filed on Oct. 27, 1999, now Pat. No. 6,348,595.
(60) Provisional application No. 60/109,610, filed on Nov. 23, 1998.

(51) Int. Cl.[7] ............................................. C07D 471/07
(52) U.S. Cl. ....................................................... 546/37
(58) Field of Search ............................................ 546/37

(56) References Cited

U.S. PATENT DOCUMENTS

| | | | | |
|---|---|---|---|---|
| 4,256,507 A | | 3/1981 | Kranz et al. ................ | 106/288 |
| 4,725,690 A | * | 2/1988 | Graser ........................ | 546/37 |
| 4,762,569 A | | 8/1988 | Miki et al. .................. | 106/476 |
| 5,207,829 A | | 5/1993 | Schwab et al. ............. | 106/493 |
| 6,348,595 B1 | * | 2/2002 | Hendi ......................... | 547/37 |

FOREIGN PATENT DOCUMENTS

| | | |
|---|---|---|
| DE | 1 444 730 | 11/1968 |
| GB | 1 225 566 | 3/1971 |

OTHER PUBLICATIONS

Derw. Abst. 1987–116736[17] of DE 1 444 730 (1968).
H. Langhals, "Cyclic Carboxylic Imide Structures as Structure Elements of High Stability. Novel Developments in Perylene Dye Chemistry", Heterocycles, vol. 40, No. 1, 1995, pp. 477–500.

* cited by examiner

*Primary Examiner*—Patricia L. Morris
(74) *Attorney, Agent, or Firm*—David R. Crichton

(57) ABSTRACT

The invention is directed to a process for preparing a bis(hydroxymethyl)perylenetetracarboximide compound by reacting perylene-3,4,9,10-tetracarboximide with formaldehyde. The bis(hydroxymethyl)perylenetetracarboximide can be isolated or further reacted in a one pot synthesis to yield a compound of the formula

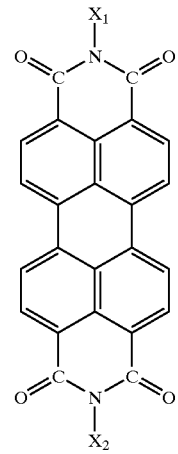

wherein $X_1$ and $X_2$ are organic radicals.

22 Claims, No Drawings

PROCESS FOR PREPARING BIS (HYDROXYMETHYL) PERYLENETETRACARBOXIMIDE

This is a divisional of application Ser. No. 09/428,101, filed Oct. 27, 1999, now U.S. Pat. No. 6,348,595 which claims the benefit under 35 U.S.C. 119(e) of U.S. Provisional Application No. 60/109,610 filed on Nov. 23, 1998.

SUMMARY

The invention relates to a process for preparing bis (hydroxymethyl) perylene-3,4,9,10-tetracarboximide wherein perylene-3,4,9,10-tetracarboximide is reacted with formaldehyde to yield the title compound, which is isolated or further reacted to form perylene derivatives which are useful as colorants for pigmenting high molecular weight organic materials.

BACKGROUND

Compounds from the class of the perylenetetracarboximides, or peryleneimides for short, have long been known in the art and are produced on an industrial scale. The compounds are recognized as being valuable colorants for high molecular weight organic materials.

U.S. Pat. No. 4,762,569 discloses N-substituted derivatives of perylene which are useful as dispersing agents for various pigments in non-aqueous media. The derivatives are prepared by reacting an amine, such as dimethylaminopropylamine methylaminopropylamine and the like, with tetracarboxylic acid dianhydride of peri-substituted condensed benzene ring of perylene. JO 1217056 discloses N-substituted derivatives of a perylene which are useful as dispersing agents for diketopyrrolopyrrole pigments in inks and paints obtained by a dispersion method. Perylene, for example, is reacted with dimethylbenzoguanamine, followed by reaction with tetrachlorophthalimide.

The present invention relates to a process for preparing a variety of N-substituted derivatives of perylene pigments wherein the N-substituents are linked to the perylene moiety by —$CH_2$— or —$CH_2$— linkages. The inventive process involves reacting perylene-3,4,9,10 -tetracarboximide with formaldehyde to yield a bis(hydroxymethyl) perylene-3,4, 9,10-tetracarboximide intermediate and further reacting the intermediate, with or without isolation, with a second reactant which reacts with the hydroxymethyl groups. The products of the reaction are useful as colorants for a variety of organic materials of high molecular weight. The bis (hydroxymethyl)perylene-3,4,9,10-tetracarboximide intermediate is useful as a colorant and as a synthon for the preparation of a variety of perylene derivatives and as a stabilizer for polymers.

DETAILED DESCRIPTION

The process according to the invention relates to a process of preparing a perylene derivative of the formula (I)

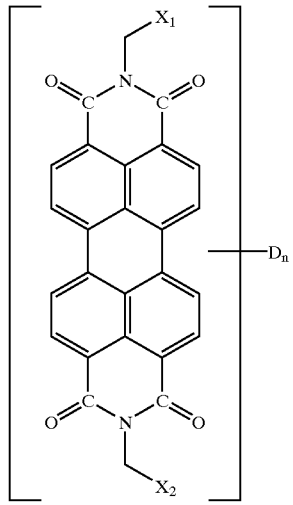

wherein $X_1$ and $X_2$, each independently of the other, are organic radcals, D is chlorine or bromine, and n is an integer from 0 to 4; which perylene derivative contains from 0 to 6 moles of —$SO_3M$ per mole of the perylene derivative, wherein M is hydrogen or a metal or ammonium cation, which process comprises reacting perylene-3,4,9,10-tetracarboximide of the formula

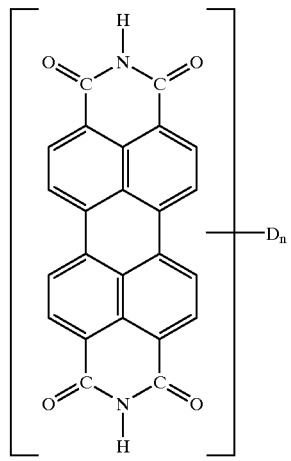

in a first step with formaldehyde to yield a sulfonated or non-sulfonated form of bis(hydroxymethyl)perylene-3,4,9, 10-tetracarboximide of the formula

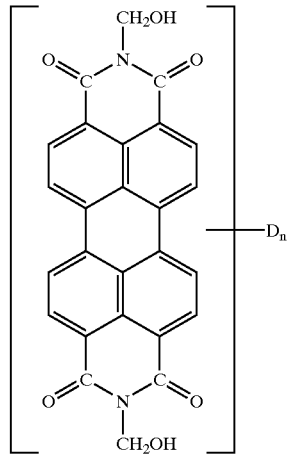

which intermidiate reacts in a second step with a precursor of the organic radicals, $X_1$ and $X_2$ to yield the sulfonated or non-sulfonated form of the perylene derivative of formula (I). In general, the second reactant reacts with the bis (hydroxymethyl)perylene-3,4,9,10-tetracarboximide by a substitution reaction or by forming an —O—linkage.

The first step is preferably carried out by adding the perylene-3,4,9,10-tetracarboximide to a solution of paraformaldehyde in oleum (fuming sulfuric acid), concentrated sulfuric acid or polyphosphoric acid. The perylene-3, 4,9,10-tetracarboximides of the above formula are known in the art and are commercially available.

When the reaction is carried out in concentrated sulfuric acid, some sulfonation occurs depending on the reaction temperature: the higher the temperature, the higher the degree of sulfonation. Reaction products containing very low to no sulfonation can be obtained under controlled conditions. The degree of sulfonation may be deliberately increased by using oleum, and the degree of sulfonation can be varied by using different reaction temperatures. Sulfur-free compounds can be easily prepared by employing polyphosphoric acid as the reaction medium.

In general, a stoichiometric amount of formaldehyde is used in the first step. It is convenient to use paraformaldehyde although anhydrous formaldehyde also serves the purpose. Thus, the molar ratio of the perylene-3,4,9,10-tetracarboximide to the formaldehyde during the first step is preferably 1:2.

After the first step is complete, the resulting bis (hydroxymethyl) intermediate is reacted with the precursor or a different substrate to yield the perylene derivatives of formula (I).

Preferably, both steps are carried out at a temperature of from 20 to 100° C. If a high degree of sulfonation is desired, the process is carried out at higher temperatures, for example above 40° C., preferably using fuming sulfuric acid. If it is desirable to have a low degree of sulfonation, the reaction is maintained at a lower temperature, preferable 40° C. or below, preferably using concentrated sulfuric acid.

When using polyphosphoric acid as the reaction medium, it is advantageous to run the reaction at a temperature of between about 50 and 180° C., preferably between about 60 and 150° C., and most preferably between about 80 and 130° C. It is advantageous to employ a ratio of 1:4 of perylene diimide to polyphosphoric acid on a weight basis, with higher ratios, i.e., 1:20 or 1:10, also being possible if necessary.

After the reaction is complete, the perylene derivative is isolated by procedures conventionally used in the art for isolating perylenes, in particular by pouring the acid solution onto ice water while maintaining the temperature below 10° C., stirring the resulting aqueous slurry, followed by filtration, washing with water and drying to yield the perylene derivative in solid form.

Since it is not necessary to isolate the intermediate, the process according to the invention is preferably a one pot process. However, it is possible to isolate the intermediate prior to carrying out the second step, especially, for example, in those instances where it is desirable to carry out the second step in a solvent other than the solvent used in the first step.

Suitable solvents for the second step include concentrated sulfuric acid, fuming sulfuric acid, polyphosphoric acid and organic solvents which do not react with the bis (hydroxymethyl) perylene-3,4,9,10-tetracarboximide intermediate, especially polar organic solvents such as acetonitrile, benzonitrile, dimethylformide, dimethylsulfoxide, tetramethylenesulfone and the like.

It is also possible to carry out the second step in a solvent which reacts with the bis(hydroxymethyl)perylene-3,4,9,10-tetracarboximide intermediate to yield the desired product. For example, $C_1$-$C_{10}$alcohols are suitable solvents if the compound of formula (I) is the ether obtainable by reacting the bis(hydroxymethyl)perylene3,4,9,10-tetracarboximide intermediate with the alcohol.

Preferably, the perylene derivatives of formula (I) contain from 0 to 4 moles of —$SO_3M$ per mole of the perylene derivative; most preferably from 0 to 2 moles per mole of perylene derivative. In general, if the reaction is carried out at about 40–50° C. in concentrated sulfuric acid, the product contains about 0 to 1.5 moles of —$SO_3M$ per mole of the perylene derivative. If the reaction is carried out at about 40–60° C. in fuming sulfuric acid, the product contains about 1 to 6 moles of —$SO_3M$ per mole of the perylene derivative, depending on the structural features of the second reactant.

M is preferably hydrogen, or an alkali metal, such as sodium or potassium, an alkaline earth metal, such as magnesium, an aluminum, a zinc or an ammonium cation. Examples of suitable ammonium cations include quaternary ammonium cations, such as trimethylcetylammonium or tributylbeneylammonium.

The organic radicals $X_1$ and $X_2$ are derivable from a precursor which reacts with the hydroxy groups of the bis(hydroxymethyl)perylene-3,4,9,10-tetracarboximide either by a substitution reaction or to form an —O— linkage.

Precursors which react with a hydroxyl group by a substitution reaction are generally compounds which comprise an aromatic radical, a heteroaromatic radical, or radicals of the formulae Q—C(=O)—Y—, —Y—C(=O)—O—Q, Q—C(=S)—Y—, —Y—C(=S)—O—Q, —Y—C(=S)—S—Q, Q—C(=N)—Y—, QZN—, Q—$SO_2NR_1$,

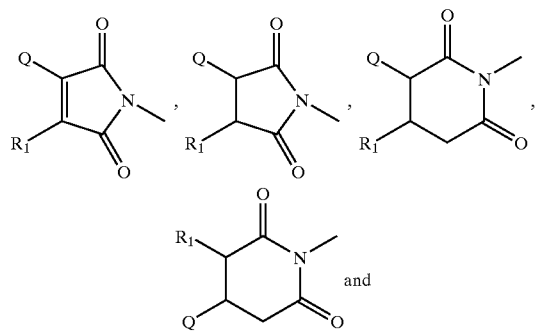

$N(R_1)$—C(=O)—O—Q; wherein Q and Z are each hydrogen or an aliphatic, alicyclic, araliphatic, aromatic or heterocyclic radical, or Q and Z together form a 3 to 8 membered ring; Y is the residue of an active methylene containing moiety; and $R_1$ is hydrogen, an aliphatic radical, an alicyclic radical, an araliphatic radical, an aromatic radical or a heterocyclic radical; or $R_1$ and Q together form a 3 to 8 membered ring.

Examples of $X_1$ and $X_2$ radicals derivable from a precursor which reacts with a hydroxyl group to form an —O— linkage include an alkyl halide and radicals of the formulae Q—C(=O)O—, Q—C(=S)O—, Q—$SO_2$—O—, QO—; wherein Q has the meaning given above.

As aromatic radicals, $X_1$ and $X_2$ especially include radicals containing 1, 2, 3, 4 or more phenyl rings which are bonded directly to each other, bonded to each other through a linking group, fused or any combination thereof. The biphenyl radical is an example of two phenyl rings directly bonded to each other. Radicals of the formulae

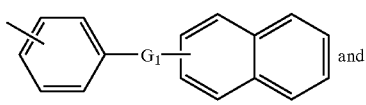

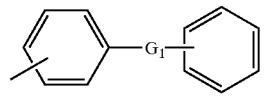

wherein $G_1$ is a linking group, are examples of phenyl rings bonded through each other through a linking group. Examples of aromatic radicals containing fused phenyl rings include naphthyl, anthyl and phenanthryl.

The linking group $G_1$ is especially —O—, $NR_2$—, N=N or —$SO_2$—.

As heteroaromatic radicals, $X_1$ and $X_2$ especially include radicals containing one or more 5, 6 or 7 membered aromatic rings containing from 1 to 4 heteroatoms. In general, the heteroatom(s) are nitrogen, oxygen, sulfur or any combination thereof. Suitable heteroaromatic radicals include the pyrrolopyrroles, especially the 1,4-diketo-3,6-diarylpyrrolo[3,4-c]pyrroles and quinacridones.

Y is the residue of an active methylene containing moiety. Active methylene moieties are generally those methylene groups which are linked to an electron withdrawing substituent, such as a carbonyl or nitrile substituent. In general, active methylene moieties participate in a Mannich type or similar reaction. In general Y is —CHQ—, —$CH_2$—Q or —CH=CH)n-$CH_2$—Q, wherein n is 1, 2 or 3. When Y is the —CHQ— radical, the —CHQ— radical is part of a ring, for example, when $X_1$ or $X_2$ is the Q—C(=O)—Y— radical, Q and Y can form part of, for example, a cyclohexanone ring.

Q and Z are aliphatic, alicyclic, araliphatic, aromatic or heterocyclic radicals.

In general aliphatic radicals include $C_1$–$C_{10}$alkyl $C_1$–$C_{10}$alkenyl and $C_1$–$C_{10}$alkynyl radicals, including straight and branched chains.

Alicyclic radicals include those moieties containing only one or more nonaromatic hydrocarbon rings. Important alicyclic radicals derived from $C_3$–$C_8$cycloalkanes and $C_3$–$C_8$cycloalkenes. Examples of important alicyclic radicals include cyclopentyl, cyclohexyl and cycloheptyl. Alicyclic radicals also include those moieties wherein there is, for example, a —C(=O)— on the ring, such as cyclohexanone.

Araliphatic radicals are those moieties which contain an aliphatic portion and an aromatic portion, for example a phenyl or heteroaromatic portion. Examples of araliphatic radicals include radicals derived from the phenylalkanoic acids, the naphthylalkanoic acids, the pyridine alkanoic acids, the quinoline alkanoic acids, the indole alkanoic acids, such as those derived from phenyl acetic acid, phenyl propionic acid or indole acetic acid.

Aromatic radicals suitable as Q and Z include those described above as being useful as $X_1$ and $X_2$. The term "aromatic" radical, in this instance, does not include heteroaromatic radicals.

Heterocyclic radicals contain one or more nonaromatic and/or aromatic rings which contain one or more heteroatoms; especially 3 to 8 membered rings which contain 1 to 3 heteroatoms, which heteroatoms are especially nitrogen, sulfur and oxygen. The term heterocyclic radical includes fused ring systems wherein one or more rings contain one or more heteroatoms. Important heterocyclic radicals include pyridinyl, pyranyl, tetrahydrofuranyl, morpholino, pyrimidyl, pyrone, oxazine, azepinyl, triazinyl, oxathiazinyl, pyrrolyl, benzofuranyl, piperazinyl oxathiazolyl, oxadiazolyl, quinolinyl, indolyl, carbazolyl, xanthenyl, acridinyl, coumarinyl, benzoxazolyl, benzopyrone, quinazolinyl. Heterocyclic radicals include those wherein the ring is a lactone or a lactam.

The description of radicals above also defines aliphatic, alicyclic, araliphatic, aromatic and heterocyclic radicals suitable as $R_1$. When $R_1$ combines with Q to form a ring, the ring is preferably a five or six membered ring.

The aromatic, heterocyclic, aliphatic, alicyclic and araliphatic radicals are unsubstituted (by any group other than hydrogen) or substituted by one or more, preferably 0 to 4, customary substituents.

Customary substituents include hydroxyl, carbonyl, halogen, $C_1$–$C_{18}$alkyl, $C_1$–$C_{18}$alkoxy, $C_1$–$C_{18}$alkylmercapto, $C_1$–$C_{18}$alkylamino, di($C_1$–$C_{18}$alkyl)amino, $C_1$–$C_{18}$alkoxycarbonyl, $C_1$–$C_{18}$alkylaminocarbonyl, —CN, —$NO_2$, trifluoromethyl, $C_5$–$C_6$cycloalkyl, —C=N—($C_1$–$C_{18}$alkyl) and phenyl, wherein the alkyl groups can be further substituted by hydroxyl, halogen, nitro, $C_1$–$C_6$alkoxy, carbonyl, —CN.

Substituents defined as halogen are typically iodo, fluoro, bromo and, preferably, chloro.

$C_1$–$C_6$Alkyl is typically methyl, ethyl, n-propyl, isopropyl, n-butyl, sec-butyl, tert-butyl, n-amyl, tert-amyl, hexyl, and $C_1$–$C_{10}$alkyl. $C_1$–$C_{18}$Allkyl are in addition typically heptyl, octyl, 2-ethylhexyl, nonyl, decyl, dodecyl, tetradecyl, hexadecyl or octadecyl.

$C_1$–$C_{18}$Alkoxy, also in $C_1$–$C_{18}$alkoxycarbonyl, is typically methoxy, ethoxy, n-propoxy, isopropoxy, butoxy, hexyloxy, decyloxy, dodecyloxy, hexadecyloxy or octadecyloxy.

$C_1$–$C_{18}$Alkylamino is, also in $C_1$–$C_{18}$alkylaminocarbonyl, typically methylamino, ethylamino, propylamino, hexylamino, decylamino, hexadecylamino or octadecylamino.

$C_5$–$C_6$Cycloalkyl is typically cyclopentyl and cyclohexyl.

Important radicals containing the residue of an active methylene, Y, include radicals derivable from various acetoacetanilides, cyanoacetanilides and benzoylacetanilides, such as ethylacetoacetate, ethyl malonate, ethyl cyanoacetate, ethyl benzoyl acetate and malononitrile.

Important radicals of the formula Q—C(=O)—O— include esters derivable from $C_1$–$C_{24}$aliphatic acids, such as acetic acid, stearic acid, oleic acid, linoleic acid, acrylic acid, methacrylic acid or trifluoroacetic acid, a $C_6$–$C_{24}$araliphatic acid, such as benzoic acid, phenyl acetic acid, phenyl propionic acid or indole acetic acid, a resin acid, such as abeitic acid, behemic acid, a naphthenic acid, a dimeric acid, wherein the aliphatic acids and araliphatic acids are unsubstituted or substituted by one or more customary substituents.

Important radicals of the formulae Q—C(=O)$NR_1$— and Q—$SO_2$—$NR_1$— include those derivable from amides and sulfonamides prepared from an aliphatic amine and an aliphatic carboxylic or sulfonic acid, an aromatic amine and an aliphatic carboxylic or sulfonic acid, or an aromatic amine and an aromatic or araliphatic carboxylic or sulfonic acid. Suitable radicals of the formulae Q—C(=O)NR$_1$ and Q—SO$_2$—NR$_1$ especially include those wherein Q is C$_1$–C$_{24}$alkyl, phenyl, benzyl, tolyl naphthyl and R$_1$ is hydrogen, methyl ethyl n-propyl isopropyl phenyl benzyl.

Important radicals of the formulae Q—SO$_2$—, Q—SO$_2$—O— and Q—C(=S)—O— include those wherein Q is a C$_1$–C$_{24}$aliphatic radical, a C$_6$–C$_{18}$aromatic radical, a C$_1$–C$_{24}$aliphatic radical, a 5, 6 or 7 membered heterocyclic ring, or a fused ring system containing a 5, 6 or 7 membered heterocyclic ring, such as pentyl, hexyl, phenyl, benzyl, tolyl naphthyl pyridinyl or indolyl. Important radicals of the formula Q—SO$_2$—O— include those derivable from p-toluene sulfonic acid, naphthalene sulfonic acid, pentane sulfonic acid or a water-soluble dye which contains an —SO$_3$H water-solubilizing group.

Important radicals of the formula QZN— include those derivable from N,N—diC$_1$–C$_{24}$alkylamines, such as dimethylamine, diethylamine, dipropylamine and dibutylamine, arylamines, such as N,N-diphenylamine, aralkylamines, such as N,N-dibenzylamine or ethylphenylamine, or heteroaryl amines, such as aminopyridine. The formula QZN— also includes those radicals wherein Q and Z, together, along with the nitrogen atom to which they are bonded, from a 3 to 8 membered ring, especially a 5 or 6 membered ring, such as piperazine, morpholine, thiomorpholine, pyrrolidone or piperidine.

Important radicals of the formula QO— include those wherein Q is a C$_1$–C$_{24}$aliphatic radical, a C$_5$–C$_{10}$alicyclic radical, phenyl, benzyl, naphthyl, or a radical H—(CH$_2$CHR$_3$O)$_m$—CH$_2$CHR$_3$—, wherein R$_3$ is hydrogen or methyl, especially hydrogen, and m is a number from 1 to 20.

Important radicals of the formula QS— include those wherein Q is a C$_1$–C$_{24}$ aliphatic radical, a C$_5$–C$_{10}$alicyclic radical, phenyl, benzyl and naphthyl.

Important radicals of the formulae

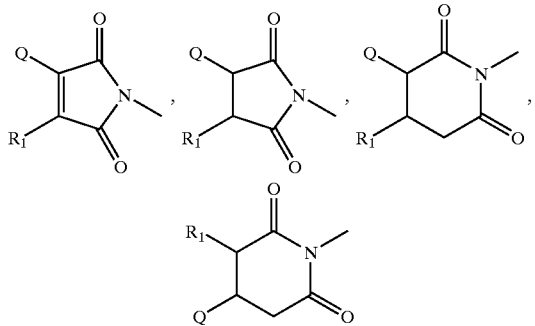

include radicals derivable form succinimide, glutarimide, phthalide, naphthalimide and isoquinoline-1,3-dione.

Important radicals of the formula —N(R$_1$)—C(=O)—O—X include those wherein R$_1$ is hydrogen, C$_1$–C$_6$alkyl, phenyl or benzyl, especially hydrogen and C$_1$–C$_6$alkyl, and Q is C$_1$–C$_6$alkyl, for example, urethane.

Aromatic and heteroaromatic radicals derivable from known dyes, such as azo, azomethine, or fiber-reactive dyes, for example triazine dyes, or known organic pigments, such as diketopyrrolopyrrole, quinacridone, phthalocyanine, indanthrone, isoindoline, isoindolone, flavanthrone, pyranthrone, anthraquinone, thioindigo, perylene and dioxazine pigments are suitable radicals for X$_1$ and X$_2$. Quinacridyl (derived from a quinacridone) and 1,4diketo-3,6-diarylpyrrolo[3,4-c]pyrrolyl (derived from a 1,4diketo-3,6-diarylpyrrolo[3,4-c]pyrrole) radicals are especially suitable radicals for X$_1$ and X$_2$.

Thus, an aspect of the present invention relates to a process of preparing perylene derivatives of the formula (I) wherein X$_1$ and X$_2$ are each a pigment moiety, in particular, a diketopyrrolopyrrole, quinacridone, phthalocyanine, indanthrone, isoindoline, isoindolone, flavanthrone, pyranthrone, anthraquinone, thioindigo, perylene or dioxazine pigment moiety.

1,4-diketo-3,6-diarylpyrrolo[3,4-c]pyrrolyl radicals are especially suitable radicals for X$_1$ and X$_2$. Such radicals are derivable from compounds of formula

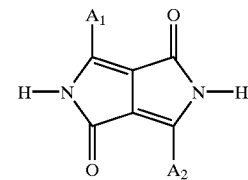

which are well known pigments.

When X$_1$ and X$_2$ are 1,4-diketo-3,6-diarylpyrrolo[3,4-c]pyrrolyl radicals, the preferences describe above for A$_1$ and A$_2$ apply.

Another aspect of the invention relates to a process for preparing perylene derivatives of formula (I) wherein X$_1$ and X$_2$ are quinacridinyl radicals. Such radicals are derivable from the compounds of the formula

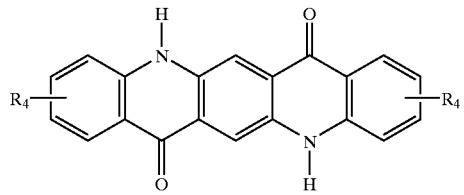

wherein each R$_4$ is independently hydrogen, halogen, carboxyl, unsubstituted C$_1$–C$_6$alkyl, C$_1$–C$_6$alkoxy which is substituted by halogen.

X$_1$ and X$_2$ are especially radicals derivable from quinacridone, 2,9-dichloroquinacridone, 4,11-dichloroquinacridone, 2,9-dimethylquinacridone, 4,11-dimethylquinacridone or 2,9-difluoroquinacridone.

The present invention also relates to the intermediate compound bis(hydroxymethyl) perylene-3,4,9,10-tetracarboximide which contains from 0 to 6 moles of —SO$_3$M per mole of said compound, wherein M is hydrogen or a metal or ammonium cation.

Preferably, the intermediate compound has from 0 to 4 moles of —SO$_3$M, most preferably from 0 to 2 moles of —SO$_3$M.

The present invention further relates to a process for preparing the intermediate compound bis(hydroxymethyl) perylene-3,4,9,10-tetracarboximide which contains from 0 to 6 moles of —SO$_3$M per mole of said compound, wherein M is hydrogen or a metal or ammonium cation, which process comprises reacting a perylene of the formula

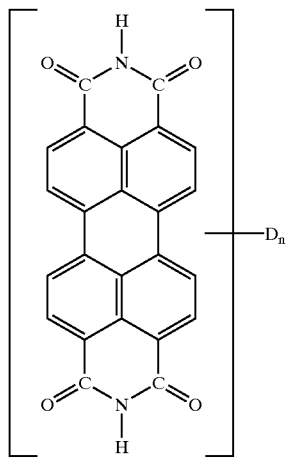

wherein D is chlorine or bromine and n is an integer from 0 to 4, with formaldehyde or paraformaldehyde.

The preferences discussed above relating to the first step of the process for preparing the intermediate compound are applicable to this aspect of the invention.

In particular, the present invention relates to the process wherein the perylene compound is combined with paraformaldehyde in concentrated sulfuric acid, oleum (fuming sulfuric acid) or polyphosphoric acid; especially wherein the perylene compound and formaldehyde are present in a molar ratio of about 0.75:2 to 1.25:2, most preferably of about 1:2.

If less sulfonation is desired, the reaction is carried out at a temperature of 40° C. or below using concentrated sulfuric acid. The reaction generally proceeds at higher temperatures, for example, in the range from about 20 to about 120° C., but higher temperatures generally lead to a higher degree of sulfonation. The use of oleum further contributes to a higher degree of sulfonation, whereas the use of concentrated sulfuric acid has been observed to result in a lower degree of sulfonation. A higher degree of sulfonation may be desirable depending on the intended use of the final product.

It is also possible to employ polyphosphoric acid in the reaction, which of coarse results in no sulfonation. It is desirable to use a sufficient amount of polyphosphoric acid such that the reactants are readily stirrable at the reaction temperature. Such amount is typically about a 1:4 weight ratio of polyphosphoric acid to reactants. It is convenient to carry out the reaction using higher amounts of polyphosphoric acid up to 10 to 20 times the weight of the reactants. It is important to maintain a reaction temperature sufficient to render the reacants readily stirrable as well as ensuring an effective condensation reaction. An effective temperature is typically on the order of from about 50 to 180° C., preferably from 60 to 150° C. and more preferably from 80 to 130° C.

The intermediate hydroxymethyl compound is generally isolated by precipitation and filtration, for example by drowning in an organic solvent or water followed by filtration.

In addition to being useful as an intermediate to prepare the perylene compounds of formula (I), the bis(hydroxymethyl)perylene-3,4,9,10-tetracarboximide is useful as a colorant and stabilizer for polymers.

The perylene derivatives of formula (I) are useful as colorants, such as pigments and dyes, for a variety of materials, in particular paints, plastics, fibers and inks, and as property enhancing agents in pigment compositions, for example as rheology improvers in paints and heat stabilizers in engineering polymers.

In general, the perylene derivatives of formula (I) with a lower degree of sulfonation are most suitable as pigments, while those with a higher degree of sulfonation are useful as dyes and additives.

The following examples are for purposes of illustration, and are not intended to limit the scope of the present invention in any manner whatsoever. Parts and percentages are by weight unless otherwise noted.

EXAMPLE 1

Bis(hydroxymethyl)perylene-3,4,9,10-tetracarboximide

Concentrated sulfuric acid (96%, 250 grams) are added to a one-liter four-necked round-bottomed flask equipped with a stirrer, thermometer and reflux condenser with a drying tube. Paraformaldehyde (1.6 grams, 0.052 mole) is then introduced into the sulfuric acid followed by the addition of small portions of perylene-3,4,9,10-tetracarboximide (9.8 grams, 0.0251 mole), maintaining the pot temperature between 40 and 45° C. The reaction mixture is stirred at 45±3° C. for 4.0 hours and then poured into ice water, filtered, washed with water until the filtrate is acid free, dried and pulverized, affording 11.1 grams (98.2% of theory) of a violet colored solid.

The isolated product analyzes as $C_{26}H_{14}N_2O_6$ corresponding to bis(hydroxymethyl)perylene-3,4,9,10-tetracarboximide.

EXAMPLE 2

Concentrated sulfuric acid (96%, 250 grams) are added to a one-liter four-necked round-bottomed flask equipped with a stirrer, thermometer and a reflux condenser with a drying tube. Paraformaldehyde (1.6 grams, 0.052 mole) is then introduced into the sulfuric acid followed by the addition of small portions of perylene-3,4,9,10-tetracarboximide (9.8 grams, 0.0251 mole), maintaining the pot temperature between 40 and 45° C. The reaction mixture is stirred at 45±3° C. for one hour to ensure complete solution. To this solution is added unsubstituted quinacridone (15.6 grams, 0.05 mole) in small portions maintaining the pot temperature below 40° C. The mixture is stirred at 45±3° C. for 3 hours, poured into ice water, filtered, washed with water until the filtrate is acid fee, dried and pulverized to yield 26.0 grams (99.7% of theory) a small particle sized maroon colored pigment.

The isolated product analyzes as $C_{66}H_{34}N_6O_8$ corresponding to the perylene diimide derivative of the formula

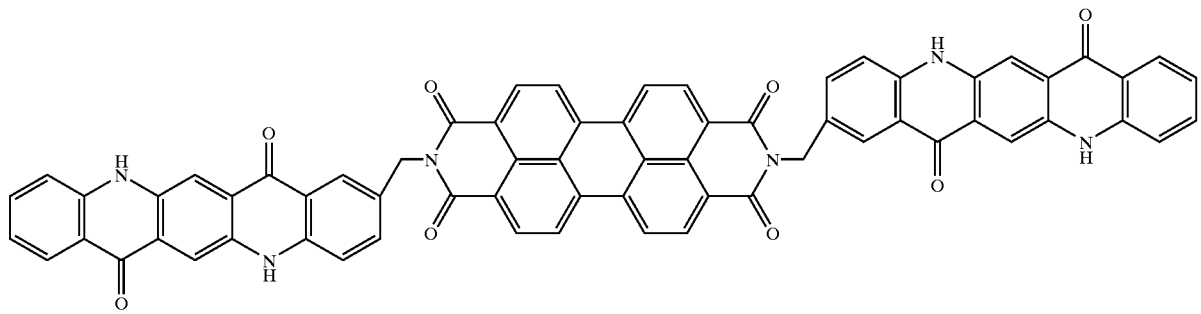

EXAMPLE 3

The same general procedure of Example 2 is followed, except using 4,11-dichloroquinacridone (19.05 grams, 0.05 mole) in place of the unsubstituted quinacridone. The product (27.0 grams, 97.1% of theory) is a small particle sized burnt orange colored pigment.

The product analyzes as $C_{66}H_{30}Cl_4N_6O_8$ corresponding to the perylene diimide derivative of the formula

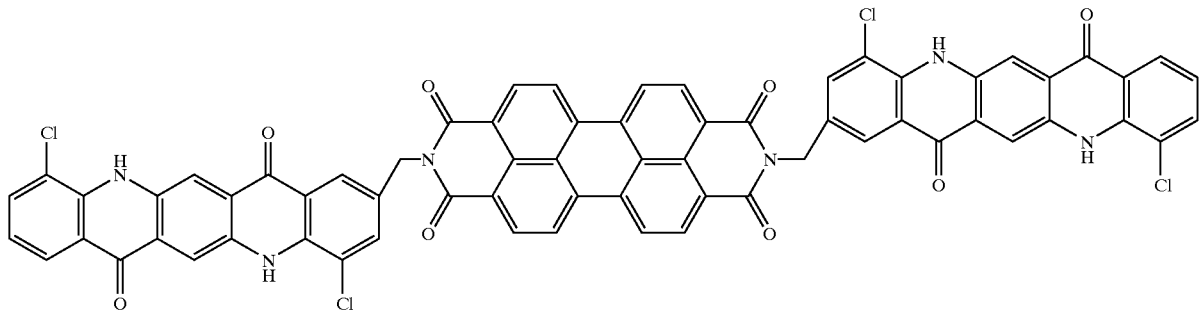

EXAMPLE 4

The same general procedure of Example 2 is followed, except using perylene-3,4,9,10-tetracarboximide (19.5 grams, 0.05 mole) in place of the unsubstituted quinacridone. The product is a small particle sized violet colored pigment obtained in quantitative yield.

The product analyzes as $C_{74}H_{30}N_6O_{12}$ corresponding to the perylene diimide derivative of the formula

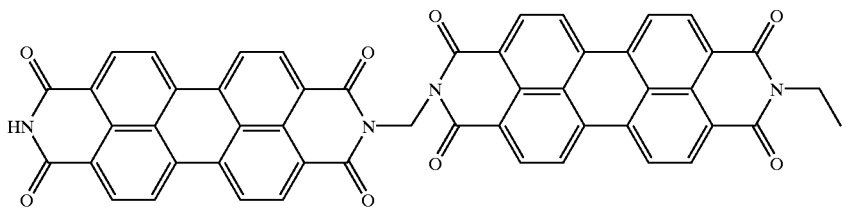

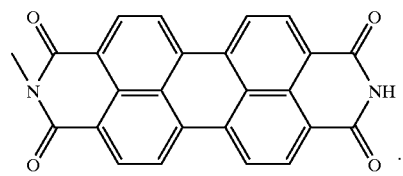

EXAMPLE 5

The same general procedure of Example 2 is followed, except using 3,6-di(4-chlorophenyl)-pyrrolo[3,4-c]pyrrol-1,4-dione (17.9 grams, 0.05 mole) in place of the unsubstituted quinacridone. The product is a small particle sized violet colored pigment obtained in quantitative yield.

The product analyzes as $C_{62}H_{30}Cl_4N_6O_8$ corresponding to the perylene diimide derivative of the formula

EXAMPLE 7

The same general procedure of Example 2 is followed, except using 3,6-di(4-tert-butylphenyl)-pyrrolo[3,4-c]pyrrol-1,4-dione (20.0 grams, 0.05 mole) in place of the unsubstituted quinacridone. The product is a small particle sized reddish violet colored pigment obtained in quantitative yield.

The product analyzes as $C_{78}H_{66}N_6O_8$ corresponding to the perylene diimide derivative of the formula

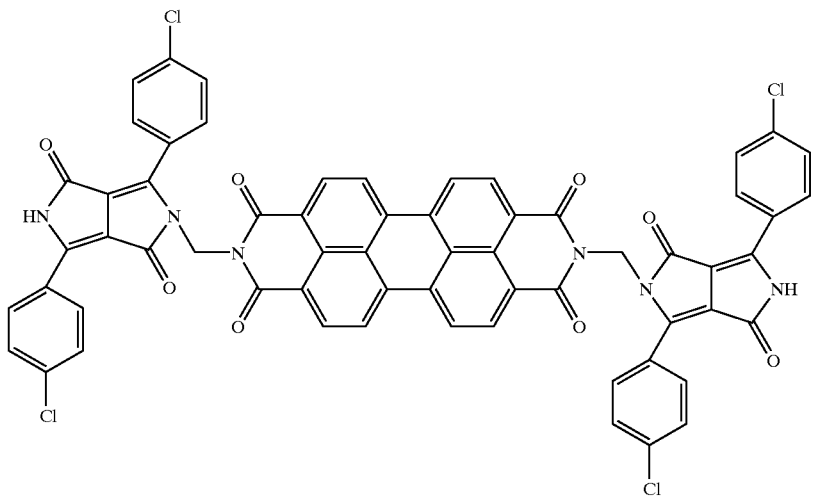

EXAMPLE 6

The same general procedure of Example 2 is followed, except using 3,6-di(4-methylphenyl)-pyrrolo[3,4-c]pyrrol-1,4-dione (15.8 grams, 0.05 mole) in place of the unsubstituted quinacridone. The product is a small particle sized reddish violet colored pigment obtained in quantitative yield.

The product analyzes as $Ca_{66}H_{42}N_6O_8$ corresponding to the perylene diimide derivative of the formula

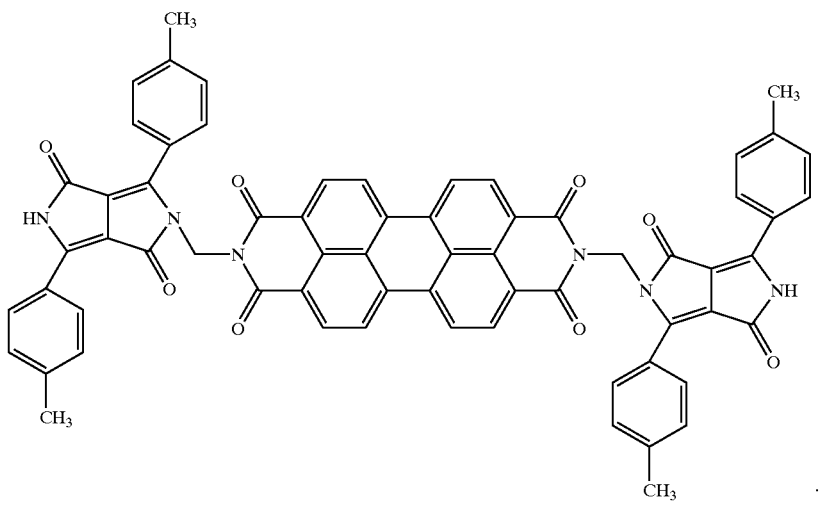

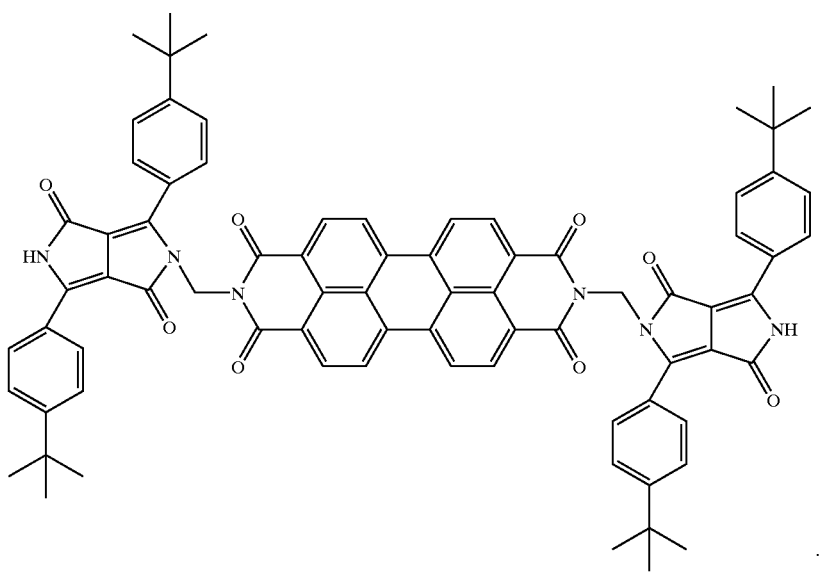

EXAMPLE 8

Fuming concentrated sulfuric acid (15% oleum with a free —SO$_3$ content of 12.0–17.0%, 250 grams) are added to a one-liter four-necked round-bottomed flask equipped with a stirrer, thermometer and a reflux condenser with a drying tube. Paraformaldehyde (1.6 grams, 0.052 mole) is then introduced into the sulfuric acid followed by the addition of small portions of perylene-3,4,9,10-tetracarboximide (9.8 grams, 0.0251 mole), maintaining the pot temperature between 40 and 45° C. The reaction mixture is stirred at 45±3° C. for one hour to ensure complete solution. To this solution is added unsubstituted quinacridone (15.6 grams, 0.05 mole) in small portions maintaining the pot temperature below 40° C. The mixture is stirred at 45±3° C. for 3 hours, poured into ice water, filtered, washed with water until the filtrate is acid fee, dried and pulverized to yield a small particle sized dark brown colored pigment (89% of theory).

Sulfur analysis for the isolated product indicates four to five sulfonic acid groups attached to the perylene diimide derivative of the formula

EXAMPLE 9

Polyphosphoric acid (115% content of H$_3$PO$_4$ from Aldrich, 300 grams) are added to a one-liter four-necked round-bottomed flask equipped with a stirrer, thermometer and a reflux condenser with a drying tube. Paraformaldehyde (1.6 grams, 0.052 mole) is then introduced into the polyphosphoric acid followed by the addition of small portions of perylene-3,4,9,10-tetracarboximide (9.8 grams, 0.0251 mole), maintaining the pot temperature between 90 and 105° C. The reaction mixture is stirred at 105±3° C. for 1.5 hours to ensure complete reaction. To this reaction mixture is added unsubstituted quinacridone (15.6 grams, 0.05 mole) in small portions maintaining the pot temperature below 120° C. The mixture is stirred at 125±3° C. for 3 hours, poured into ice water, filtered, washed with water until the filtrate is acid fee, dried and pulverized to yield a small particle sized maroon colored pigment obtained in quantitative yield.

The isolated product analyzes as C$_{66}$H$_{34}$N$_6$O$_8$ corresponding to the perylene diimide derivative of the formula

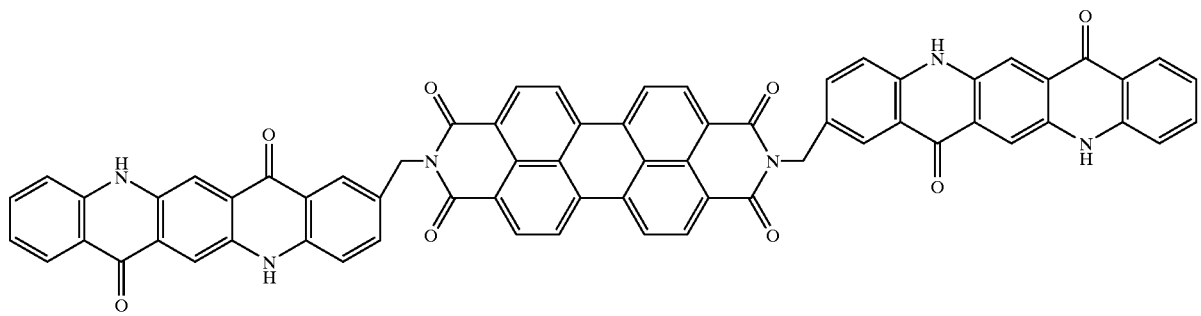

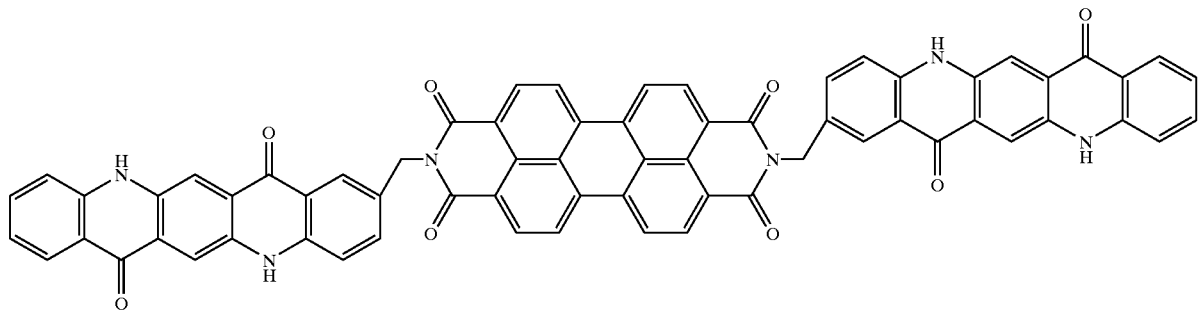

What is claimed is:

1. A process for the preparation of a perylene derivative of the formula (I)

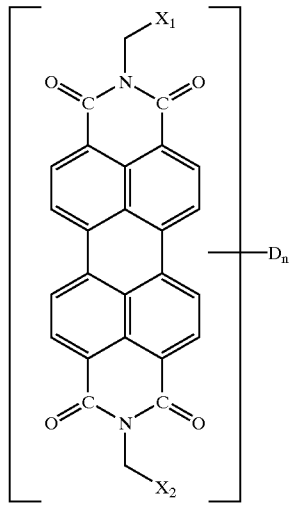

wherein $X_1$ and $X_2$, each independently of the other, are pigment moieties selected from the group consisting of diketopyrrolopyrrole, quinacridone, phthalocyanine, indanthrone, isoindoline, isoindolone, flavanthrone, pyranthrone, anthraquinone, thioindigo, perylene and dioxazine moieties and mixtures thereof, D is chlorine or bromine, and n is an integer from 0 to 4; which perylene derivative contains from 0 to 6 moles of —$SO_3M$ per mole of the perylene derivative; wherein M is hydrogen or a metal or ammonium cation, which process comprises reacting perylene-3,4,9,10-tetracarboximide of the formula

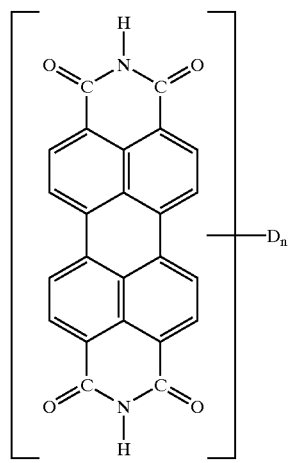

in a first step with formaldehyde to yield a sulfonated or non-sulfonated form of bis(hydroxymethyl)perylene-3,4,9,10-tetracarboximide of the formula (II)

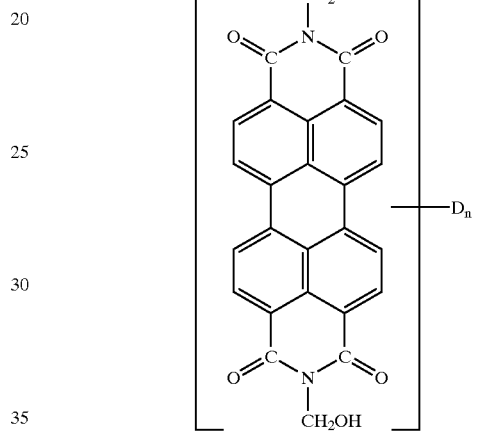

which intermediate reacts in a second step with a precursor of the organic radicals, $X_1$ and $X_2$, to yield the sulfonated or non-sulfonated form of the perylene derivative of formula (I).

2. The process of claim 1 wherein the precursor reacts with the hydroxy groups of the intermediate of formula (II) by a substitution reaction or to form an —O— linkage.

3. The process of claim 1 wherein the perylene-3,4,9,10-tetracarboximide and formaldehyde are present in a molar ratio of about 1:2.

4. The process of claim 1 wherein the first step is carried out by combining the perylene-3,4,9,10-tetracarboximide with formaldehyde in concentrated sulfuric acid.

5. The process of claim 4 wherein the process is carried out at a temperature of 40° C. or below.

6. The process of claim 1 wherein the first step is carried out by combining the perylene-3,4,9,10-tetracarboximide with formaldehyde in oleum.

7. The process of claim 6 wherein the process is carried out at a temperature of 40° C. or above.

8. The process of claim 1 wherein the first step is carried out by combining the perylene-3,4,9,10-tetracarboximide with formaldehyde in polyphosphoric acid.

9. The process of claim 8 wherein the process is carried out at a temperature of between 50 and 180° C.

10. The process of claim 1 wherein the second step is carried out without isolating the intermediate of formula (II).

11. The process of claim 1 wherein the intermediate of formula (II) is isolated prior to carrying out the second step.

12. The process of claim 1 wherein the perylene derivative of formula (I) contains from 0 to 4 moles of —SO$_3$M per mole of the perylene derivative.

13. The process of claim 1 wherein the perylene derivative of formula (I) contains from 0 to 2 moles of —SO$_3$M per mole of the perylene derivative.

14. The process of claim 1 wherein the precursor of the organic radicals, X$_1$ and X$_2$, is a 1,4-diketo-3,6-diarylpyrrolo[3,4-c]pyrrole, a quinacridone or a perylene-3,4,9,10-tetracarboximide, or a mixture thereof.

15. The process of claim 1 wherein n is 0.

16. A compound of the formula (II)

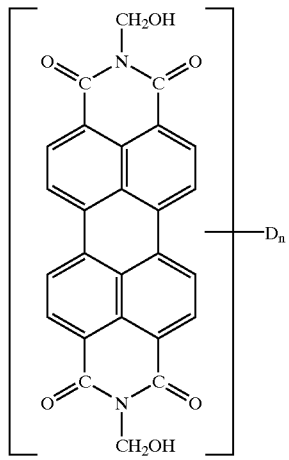

having from 0 to 6 moles of —SO$_3$M per mole of the compound, wherein D is chlorine or bromine and n is an integer from 0 to 4 and M is hydrogen or a metal or ammonium cation.

17. The compound of claim 16 wherein n is 0.

18. The compound of claim 16 having from 0 to 4 moles of —SO$_3$M per mole of the compound.

19. The compound of claim 16 having from 0 to 2 moles of —SO$_3$M per mole of the compound.

20. A process according to claim 1 wherein X$_1$ and X$_2$ are 1,4-diketo-3,6-diarylpyrrolo[3,4-c]pyrrolyl radicals.

21. A process according to claim 1 wherein X$_1$ and X$_2$ are quinacridinyl radicals derived from the compounds of the formula

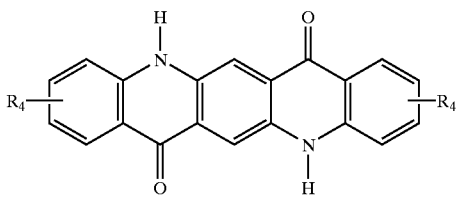

wherein each R$_4$ is independently hydrogen, halogen, carboxyl, unsubstituted C$_1$–C$_6$alkyl, C$_1$–C$_6$alkoxy which is substituted by halogen.

22. A process according to claim 21 wherein X$_1$ and X$_2$ are radicals derived from quinacridone, 2,9-dichloroquinacridone, 4,11-dichloroquinacridone, 2,9-dimethylquinacridone, or 4,11-dimethylquinacridone or 2,9-difluoroquinacridone.

* * * * *